United States Patent
Souvie et al.

(10) Patent No.: US 7,498,465 B2
(45) Date of Patent: *Mar. 3, 2009

(54) PROCESS FOR THE SYNTHESIS AND CRYSTALLINE FORM OF AGOMELATINE

(75) Inventors: Jean-Claude Souvie, Le Havre (FR); Isaac Gonzalez Blanco, Toledo (ES); Gilles Thominot, Normanville (FR); Genevieve Chapuis, Orleans (FR); Stephane Horvath, Lachapelle-Saint-Mesmin (FR); Gerard Damien, Meung-sur-Loire (FR)

(73) Assignee: Les Laboratoires Servier, Courbevoie Cedex (FR)

( * ) Notice: Subject to any disclaimer, the term of this patent is extended or adjusted under 35 U.S.C. 154(b) by 0 days.

This patent is subject to a terminal disclaimer.

(21) Appl. No.: 11/807,941

(22) Filed: May 30, 2007

(65) Prior Publication Data

US 2008/0004347 A1    Jan. 3, 2008

Related U.S. Application Data

(63) Continuation-in-part of application No. 11/052,630, filed on Feb. 7, 2005, now Pat. No. 7,250,531.

(30) Foreign Application Priority Data

Feb. 13, 2004    (FR) .................................... 04 01439

(51) Int. Cl.
*C07C 233/05*    (2006.01)
*A61K 31/165*    (2006.01)

(52) U.S. Cl. ..................................... 564/172; 514/617
(58) Field of Classification Search ................. 564/172; 514/617

See application file for complete search history.

(56) References Cited

U.S. PATENT DOCUMENTS

| | | | |
|---|---|---|---|
| 3,931,188 A | 1/1976 | Douglas et al. | |
| 3,992,403 A | 11/1976 | Roebke | |
| 7,250,531 B2 * | 7/2007 | Souvie et al. | 564/172 |
| 2005/0164987 A1 * | 7/2005 | Barberich | 514/58 |

FOREIGN PATENT DOCUMENTS

EP    0447285    9/1991

OTHER PUBLICATIONS

French Search Report for French Application No. 04.01439, Sep. 15, 2004.
European Search Report for European Application No. 05290308, May 20, 2005.
International Search Report for International Application No. PCT/FR2005/000327, Jun. 16, 2005.
Depreux, et al., *J. Med. Chem.*, 1994, 37, 3231-3239.
Tinant, et al., *Acta. Cryst.*, 1994, C50, 907-910.

* cited by examiner

*Primary Examiner*—Shailendra Kumar
(74) *Attorney, Agent, or Firm*—Hueschen and Sage

(57) ABSTRACT

A process for the industrial synthesis and new crystalline form of the compound of formula (I):

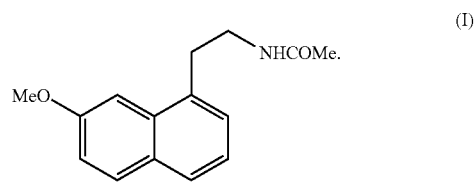

Medicinal products containing the same which are useful in treating disorders of the melatoninergic system.

3 Claims, No Drawings

PROCESS FOR THE SYNTHESIS AND CRYSTALLINE FORM OF AGOMELATINE

This application is a CIP of Ser. No. 11/052,630, filed Feb. 7, 2005, now U.S. Pat. No. 7,250,531.

FIELD OF THE INVENTION

The present invention relates to a process for the industrial synthesis of agomelatine, or N-[2-(7-methoxy-1-naphthyl)ethyl]acetamide, of formula (I):

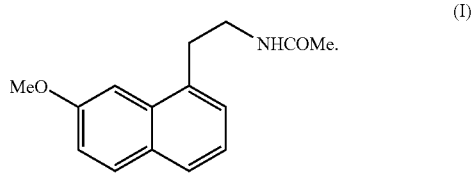

The present invention relates also to crystalline form II of agomelatine, a process for its preparation and pharmaceutical compositions containing it.

BACKGROUND OF THE INVENTION

Agomelatine, or N-[2-(7-methoxy-1-naphthyl)ethyl]acetamide, has valuable pharmacological properties.

Indeed it has the double feature of being, on the one hand, an agonist of melatoninergic system receptors and, on the other hand, an antagonist of the 5-HT$_{2C}$ receptor. Those properties confer activity in the central nervous system and, more especially, in the treatment of severe depression, seasonal affective disorders, sleep disorders, cardiovascular pathologies, pathologies of the digestive system, insomnia and fatigue resulting from jetlag, appetite disorders and obesity.

DESCRIPTION OF THE PRIOR ART

Agomelatine, its preparation and its therapeutic use have been described in European Patent Specification EP 0 447 285.

In view of the pharmaceutical value of this compound, it has been important to be able to obtain it by an effective industrial synthesis process that is readily transposable to an industrial scale and that results in agomelatine in a good yield and with excellent purity.

It has been also important to be able to obtain agomelatine with well defined crystalline form, perfectly reproducible, which as a result exhibits valuable characteristics in terms of filtration and ease of formulation.

Patent Specification EP 0 447 285 describes the preparation of agomelatine in eight steps, starting from 7-methoxy-1-tetralone, giving an average yield of less than 30%.

That process involves the action of ethyl bromoacetate, followed by aromatisation and saponification to yield the corresponding acid, which is then converted to acetamide and subsequently dehydrated to yield (7-methoxy-1-naphthyl)acetonitrile, this being followed by reduction, and then condensation of the acetyl chloride.

In particular, the preparation of (7-methoxy-1-naphthyl)acetonitrile involves six reaction steps and, transposed to an industrial scale, has quickly demonstrated the difficulties of carrying out the process, these being caused principally by problems of reproducibility of the first step, which constitutes the action of ethyl bromoacetate on 7-methoxy-1-tetralone according to the Réformatsky reaction resulting in ethyl (7-methoxy-3,4-dihydro-1(2H)-naphthalenylidene)ethanoate.

Moreover, the subsequent step of aromatisation of ethyl (7-methoxy-3,4-dihydro-1(2H)-naphthalenylidene)ethanoate has often been incomplete and resulted, after saponification, in a mixture of products that is difficult to purify.

The literature describes obtaining (7-methoxy-1-naphthyl)acetonitrile in three steps starting from 7-methoxy-1-tetralone, by the action of LiCH$_2$CN followed by dehydrogenation with DDQ (2,3-dichloro-5,6-dicyano-1,4-benzoquinone) and finally dehydration in acid medium (Synthetic Communication, 2001, 31(4), 621-629). The total yield is mediocre (76%), however, and in particular the DDQ used in the dehydrogenation reaction and the benzene reflux necessary in the third step do not comply with industrial requirements in terms of cost and the environment.

DETAILED DESCRIPTION OF THE INVENTION

The Applicant has now developed a new industrial synthesis process that results, in a reproducible manner and without the need for laborious purification, in agomelatine of a purity compatible with its use as a pharmaceutical active ingredient.

An alternative to the difficulties encountered with the process described in Patent Specification EP 0 447 285 has been obtained by directly condensing a cyano compound with 7-methoxy-1-tetralone. It was in addition necessary that the condensation compound obtained could readily be subjected to aromatisation to yield (7-methoxy-1-naphthyl)acetonitrile without the need for drastic conditions, and that reagents compatible with industrial requirements in terms of cost and the environment could be used.

It is apparent that (7-methoxy-3,4-dihydro-1-naphthalenyl)acetonitrile would constitute an ideal synthesis intermediate that meets the requirements for direct synthesis from 7-methoxy-1-tetralone, and would be an excellent substrate for the aromatisation step.

Reactions for the direct condensation of tetralones with acetonitrile or acetonitrile compounds are described in the literature. In particular, U.S. Pat. No. 3,992,403 describes the condensation of cyanomethyl phosphonate with 6-fluoro-1-tetralone, and U.S. Pat. No. 3,931,188 describes the condensation of acetonitrile with tetralone leading to a cyano intermediate which is directly engaged in the subsequent reaction. Applied to 7-methoxy-1-tetralone, the condensation of acetonitrile yields a mixture of isomers in which "exo" constitutes the major portion and "endo" the minor portion, according to FIG. 1:

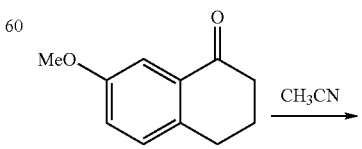

FIG. 1

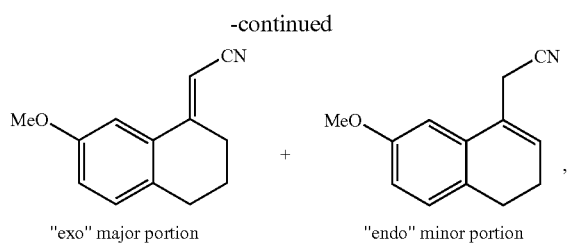

"exo" major portion     "endo" minor portion such a mixture requiring subsequent drastic aromatisation conditions that are not compatible with the industrial requirements for the purpose of carrying out the synthesis of agomelatine.

The Applicant has now developed a new industrial synthesis process that allows (7-methoxy-1-naphthyl)acetonitrile to be obtained from 7-methoxy-tetralone, in a reproducible manner and without the need for laborious purification, in only two steps by using as synthesis intermediate (7-methoxy-3,4-dihydro-1-naphthalenyl)acetonitrile free from the "exo" impurity of formula (II):

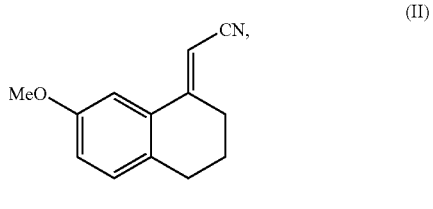

(II)

which impurity cannot be subjected to subsequent aromatisation under operating conditions that are compatible with the industrial requirements for the purpose of carrying out the synthesis of agomelatine.

More specifically, the present invention relates to a process for the industrial synthesis of the compound of formula (I):

(I)

which is characterised in that 7-methoxy-1-tetralone of formula (III):

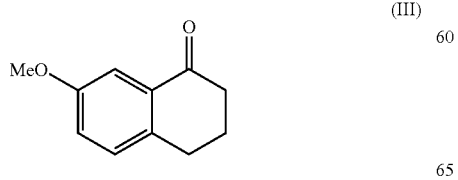

(III)

is reacted with cyanoacetic acid of formula (IV):

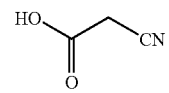

(IV)

in conditions wherein the water formed is removed, in the presence of a catalytic amount of a compound of formula (V):

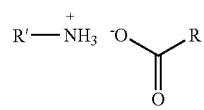

(V)

wherein R and R', which may be the same or different, each represents a linear or branched ($C_3$-$C_{10}$)alkyl group, an unsubstituted or substituted aryl group, or an unsubstituted or substituted linear or branched aryl ($C_1$-$C_6$)alkyl group, to yield, after filtration and washing with a basic solution, (7-methoxy-3,4-dihydro-1-naphthalenyl)acetonitrile of formula (VI):

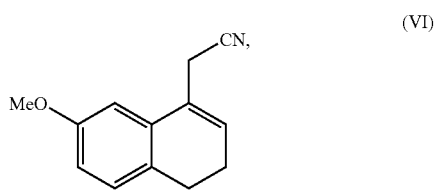

(VI)

which compound of formula (VI) is reacted with a hydrogenation catalyst in the presence of an allyl compound to yield the compound of formula (VII):

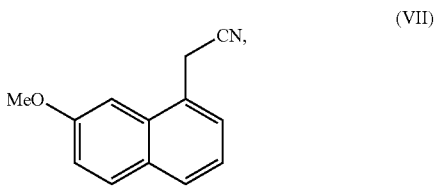

(VII)

which is then subjected to reduction with hydrogen in the presence of Raney nickel in ammoniacal ethanol medium, and subsequently converted to a salt using hydrochloric acid to yield the compound of formula (VIII):

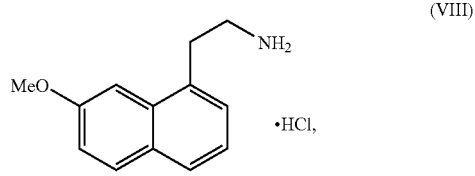

(VIII)

which is subjected successively to the action of sodium acetate and then acetic anhydride to yield the compound of formula (I), which is isolated in the form of a solid wherein:
aryl is understood to mean a phenyl, naphthyl or biphenyl group, the term "substituted" governing the terms "aryl" and "arylalkyl" denotes that the aromatic moiety of those groups may be substituted by from 1 to 3 identical or different groups selected from linear or branched $(C_1-C_6)$alkyl, hydroxy and linear or branched $(C_1-C_6)$alkoxy, "allyl compound" is understood as any molecule containing from 3 to 10 carbon atoms, which may contains in addition 1 to 5 oxygen atoms, and containing at least one —$CH_2$—$CH$=$CH_2$ group.

More especially, in the reaction for the conversion of the compound of formula (III) to a compound of formula (VI), the water formed is removed by distillation. There is preferably used a reaction solvent that has a boiling temperature higher than or equal to that of water, and even more preferably that forms an azeotrope with water, such as, for example, xylene, toluene, anisole, ethylbenzene, tetrachloroethylene, cyclohexene or mesitylene.

Preferably, the conversion of the compound of formula (III) to the compound of formula (VI) is carried out with reflux of toluene or xylene and, more especially, with reflux of toluene.

In the reaction for the conversion of the compound of formula (III) to a compound of formula (VI), advantageously one of the groups R or R' of the catalyst employed represents a linear or branched $(C_3-C_{10})$alkyl group and the other represents an aryl or arylalkyl group. More especially, a preferred catalyst is that of formula $(V_a)$:

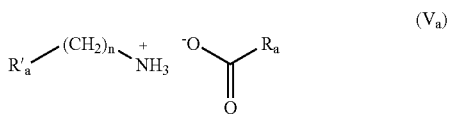

(Va)

wherein R'$_a$ represents a phenyl group unsubstituted or substituted by one or more linear or branched $(C_1-C_6)$alkyl groups, n is 0 or 1, and $R_a$ represents a linear $(C_3-C_{10})$alkyl group.

Advantageously, R'$_a$ represents an unsubstituted or substituted phenyl group, more especially an unsubstituted phenyl group.

The preferred group $R_a$ is the hexyl group.

The preferred value of n is 1.

The preferred catalyst used in the conversion of the compound of formula (III) to the compound of formula (VI) according to the process of the invention is benzylammonium heptanoate of formula (IX):

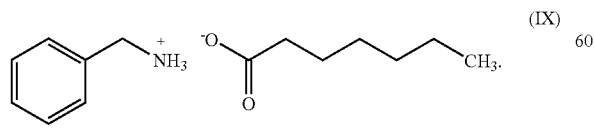

(IX)

Advantageously, the compound of formula (VI) is obtained after filtration and washing with a mineral or organic basic solution, such as NaOH, KOH, Ca(OH)$_2$, Sr(OH)$_2$ or NH$_4$OH, and more especially with a sodium hydroxide solution.

Preferably, the conversion of the compound of formula (VI) to the compound of formula (VII) is carried out with reflux of toluene or xylene, more especially with reflux of toluene.

The catalyst preferably used in the conversion of the compound of formula (VI) to the compound of formula (VII) is a catalyst either in oxide form or supported as for example palladium, platinum, nickel, Al$_2$O$_3$ and, more especially, palladium. Advantageously, 1 to 20% palladium-on-carbon will be used, and more particularly 5% or 10% palladium-on-carbon. Preferably, palladium-on-carbon will be used in amounts ranging from 1 to 10% by weight of catalyst in relation to the weight of substrate, and more especially 5%. The hydrogen acceptor preferably used in the reaction for the conversion of the compound of formula (VI) to a compound of formula (VII) is an allyl compound and, more especially, an allyl acrylate or an allyl glycidyl ether. The preferred allyl acrylate of the process according to the invention is allyl methacrylate.

Advantageously, the conversion of the compound of formula (VII) to the compound of formula (VIII) according to the process of the invention is carried out at from 20 to 40° C., more especially at from 30 and 40° C., and even more advantageously at 40° C.

Advantageously, the conversion of the compound of formula (VIII) to the compound of formula (I) is carried out in alcoolic medium and more particularly in an ethanolic medium.

This process is of particular interest for the following reasons:
it allows the "endo" compound of formula (VI), exclusively, to be obtained on an industrial scale. This result is altogether surprising considering the literature relating to that type of reaction, which most frequently reports obtaining "exo"/"endo" mixtures (Tetrahedron, 1966, 22 3021-3026). The result is due to the use of a compound of formula (V) as reaction catalyst instead of the ammonium acetates currently used in such reactions (Bull. Soc. Chim. Fr., 1949, 884-890).

the rate of conversion of the compound of formula (III) to the compound of formula (VI) is very high, exceeding 97%, unlike that which could be observed using acetic acid, for which the rate does not exceed 75%.

the use of a hydrogenation catalyst in the presence of an allyl compound for the conversion of the compound of formula (VI) to the compound of formula (VII) is entirely compatible with industrial requirements in terms of cost and the environment, unlike the quinones currently used.

furthermore, it allows the compound of formula (VII), exclusively, in particular free from the corresponding reduction product of formula (X):

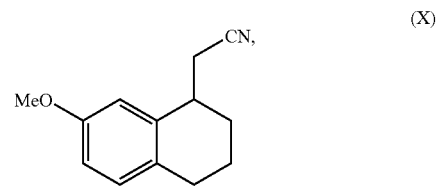

(X)

to be obtained on an industrial scale.

finally, the observed rates of conversion of the compound of formula (VI) to the compound of formula (VII) are high, exceeding 90%.

hydrogenation of the compound of formula (VII) in the presence of Raney nickel in ammoniacal ethanol medium has been described (J. Med. Chem., 1994, 37(20), 3231-3239), but requires conditions that are difficult to apply to an industrial scale: the reaction is carried out at 60° C. and for 15 hours, and the final yield is less than 90%. Furthermore, a principal drawback of that reaction is the concomitant formation of the "bis" compound of formula (XI):

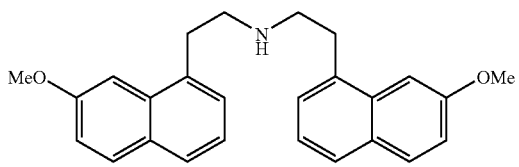

(XI)

and the difficulty of controlling the conversion rate of that impurity. The process developed by the Applicant allows the compound of formula (VIII) to be obtained with a level of impurity down to below 4% under experimental conditions that are compatible with industrial requirements, since the reaction is carried out at from 30 to 40° C. to give a yield exceeding 90% and a chemical purity exceeding 99.5%.

the amidation step carried out in alcoolic medium and more particularly in an ethanolic medium allows the compound of formula (I) to be isolated very easily in a quantitative yield, a result which is completely surprising since a reaction of that type is not very compatible with that solvent, for which a competitive consumption of acetic anhydride would be expected.

The compound of formula (VI) obtained according to the process of the invention is new and is useful as an intermediate in the synthesis of agomelatine, in which it is subjected to aromatisation followed by reduction and then to coupling with acetic anhydride.

The invention relates also to the crystalline II form of agomelatine obtained according to the process described above. It is, in fact, important to be able to obtain a well defined and perfectly reproducible crystalline form.

The prior art EP 0 447 285 and Yous et al. (Journal of Medicinal Chemistry, 1992, 35 (8), 1484-1486) allows agomelatine to be obtained in a particular crystalline form which has been described in Tinant et al. (Acta Cryst., 1994, C50, 907-910).

The Applicant has now developed a process for obtaining agomelatine in a well-defined, perfectly reproducible, crystalline form and which as a result exhibits valuable characteristics in terms of filtration and ease of formulation.

More specifically, the present invention relates to the crystalline II form of agomelatine, characterised by the following parameters, obtained from the powder diagram obtained using a Bruker AXS D8 high-resolution diffractometer having a 2θ angular range of 3°-90°, a step of 0.01° and 30 s per step:

monoclinic crystal lattice
lattice parameters: a=20.0903 Å, b=9.3194 Å, c=15.4796 Å, β=108.667°
space group : $P2_1/n$
number of molecules in the unit cell: 8
unit cell volume: $V_{unit\ cell}$=2746.742 Å$^3$
density: d=1.13 g/cm$^3$.

The crystalline form II of agomelatine of the present invention may also be characterised by the following powder X-ray diffraction data, measured using a diffractometer (copper anticathode) and expressed in terms of inter-planar distance d (expressed in Å), Bragg's angle 2 theta (expressed in degrees), and relative intensity (expressed as a percentage with respect to the most intense ray):

| Angle 2 theta (°) | Inter-planar distance d (Å) | Intensity (%) |
|---|---|---|
| 6.30 | 14.009 | 15 |
| 9.26 | 9.544 | 23 |
| 10.50 | 8.419 | 13 |
| 12.65 | 6.995 | 50 |
| 13.29 | 6.655 | 13 |
| 15.34 | 5.771 | 24 |
| 15.81 | 5.599 | 16 |
| 17.15 | 5.165 | 100 |
| 18.03 | 4.917 | 16 |
| 18.60 | 4.766 | 72 |
| 19.01 | 4.665 | 75 |
| 20.09 | 4.417 | 77 |
| 20.44 | 4.343 | 38 |
| 20.97 | 4.234 | 12 |
| 21.18 | 4.191 | 15 |

An advantage of obtaining that crystalline form is that it allows especially rapid and efficient filtration as well as the preparation of pharmaceutical formulations having a consistent and reproducible composition, which is especially advantageous when the formulations are to be used for oral administration.

The form so obtained is sufficiently stable to enable prolonged storage without special conditions in respect of temperature, light humidity or oxygen levels.

A pharmacological study of the form so obtained has demonstrated that it has substantial activity in respect of the central nervous system and in respect of microcirculation, enabling it to be established that the crystalline II form of agomelatine is useful in the treatment of stress, sleep disorders, anxiety, severe depression, seasonal affective disorders, cardiovascular pathologies, pathologies of the digestive system, insomnia and fatigue due to jetlag, schizophrenia, panic attacks, melancholia, appetite disorders, obesity, insomnia, pain, psychotic disorders, epilepsy, diabetes, Parkinson's disease, senile dementia, various disorders associated with normal or pathological ageing, migraine, memory loss, Alzheimer's disease, and in cerebral circulation disorders. In another field of activity, it appears that the crystalline II form of agomelatine can be used in the treatment of sexual dysfunction, that it has ovulation-inhibiting and immunomodulating properties and that it lends itself to use in the treatment of cancers.

The crystalline II form of agomelatine will preferably be used in the treatment of severe depression, seasonal affective disorders, sleep disorders, cardiovascular pathologies, insomnia and fatigue due to jetlag, appetite disorders and obesity.

The invention relates also to pharmaceutical compositions comprising as active ingredient the crystalline II form of agomelatine together with one or more appropriate inert, non-toxic excipients. Among the pharmaceutical compositions according to the invention there may be mentioned, more especially, those which are suitable for oral, parenteral (intravenous or subcutaneous) or nasal administration, tablets or dragees, granules, sublingual tablets, gelatin capsules, lozenges, suppositories, creams, ointments, dermal gels, injectable preparations, drinkable suspensions and disintegrable pastes.

The useful dosage can be adapted according to the nature and the severity of the disorder, the administration route and the age and weight of the patient. The dosage varies from 0.1 mg to 1 g per day in one or more administrations.

The Examples below illustrate the invention but do not limit it in any way.

EXAMPLE 1

N-[2-(7-Methoxy-1-naphthyl)ethyl]acetamide

Step A: (7-Methoxy-3,4-dihydro-1-naphthalenyl)acetonitrile

There are introduced into a 670 litre reactor 85.0 kg of 7-methoxy-1-tetralone, 60.3 kg of cyanoacetic acid and 15.6 kg of heptanoic acid in toluene in the presence of 12.7 kg of benzylamine. The mixture is heated at reflux. When all the starting substrate has disappeared, the solution is cooled and filtered. The precipitate obtained is washed with toluene and then the filtrate obtained is washed with a 2N sodium hydroxide solution and subsequently with water until neutral. After removal of the solvent by evaporation, the resulting solid is recrystallised from an ethanol/water (80/20) mixture to give the title product in a yield of 90% and with a chemical purity exceeding 99%.

Melting point: 48-50° C.

Step B: (7-Methoxy-1-naphthyl)acetonitrile

There are introduced into a 670 litre reactor 12.6 kg of 5% palladium-on-carbon in toluene, which is heated at reflux; then 96.1 kg of (7-methoxy-3,4-dihydro-1-naphthalenyl)-acetonitrile dissolved in toluene are added as well as 63.7 kg of allyl methacrylate. The reaction is continued at reflux and is followed by vapour phase chromatography. When all the starting substrate has disappeared, the reaction mixture is cooled to ambient temperature and then filtered. After removal of the toluene by evaporation, the resulting solid residue is recrystallised from an ethanol/water (80/20) mixture to give the title product in a yield of 91% and with a chemical purity exceeding 99%.

Melting point: 83° C.

Step C: 2-(7-Methoxy-1-naphthyl)ethanamine Hydrochloride

There are introduced into a 1100 litre reactor 80.0 kg of the compound obtained in Step B, 24.0 kg of Raney nickel in ethanol and 170 l of ammonium hydroxide. The mixture is stirred under a hydrogen pressure of 30 bars, then brought to 40° C. When all the starting substrate has disappeared, the solvent is evaporated off, the resulting residue is redissolved in ethyl acetate, and 41.5 l of an 11N hydrochloric acid solution are added. After filtration, the precipitate obtained is washed with ethyl acetate and then dried in an oven to give the title product in a yield of 95.3% and with a chemical purity exceeding 99.5%.

Melting point: 243° C.

Step D: N-[2-(7-Methoxy-1-naphthyl)ethyl]acetamide 173 kg of the compound obtained in Step C and 66 kg of sodium acetate in ethanol are introduced into a 1600 litre reactor. The mixture is stirred and then 79 kg of acetic anhydride are added; the reaction mixture is heated at reflux and 600 l of water are added. The reaction mixture is allowed to return to ambient temperature and the precipitate obtained is filtered off and washed with a 35/65 ethanol/water mixture to give the title product in a yield of 92.5% and with a chemical purity exceeding 99%.

Melting point: 108° C.

EXAMPLE 2

N-[2-(7-Methoxy-1-naphthyl)ethyl]acetamide

Step A: (7-Methoxy-3,4-dihydro-1-naphthalenyl)acetonitrile

There are introduced into a 670 litre reactor 85.0 kg of 7-methoxy-1-tetralone, 60.3 kg of cyanoacetic acid and 15.6 kg of heptanoic acid in toluene in the presence of 11.0 kg of aniline. The mixture is heated at reflux. When all the starting substrate has disappeared, the solution is cooled and filtered. The precipitate obtained is washed with toluene and then the filtrate obtained is washed with a 2N sodium hydroxide solution and subsequently with water until neutral. After removal of the solvent by evaporation, the resulting solid is recrystallised from an ethanol/water (80/20) mixture to give the title product in a yield of 87% and with a chemical purity exceeding 99%.

Melting point: 48-50° C.

Step B: (7-Methoxy-1-naphthyl)acetonitrile

The procedure is as in Step B of Example 1.

Melting point: 83° C.

Step C: 2-(7-Methoxy-1-naphthyl)ethanamine Hydrochloride

The procedure is as in Step C of Example 1.

Melting point. 243° C.

Step D: N-[2-(7-Methoxy-1-naphthyl)ethyl]acetamide

The procedure is as in Step D of Example 1.

Melting point: 108° C.

EXAMPLE 3

Crystalline II form of N-[2-(7-methoxy-1-napthyl)ethyl]acetamide

Data recording was carried out using a Bruker AXS D8 high-resolution diffractometer with the following parameters: a 2θ angular range of 3°-90°, a step of 0.01° and 30 s per step. The N-[2-(7-methoxy-1-napthyl)ethyl]acetamide powder obtained in Example 1 was deposited on a transmission mounting support. The X-ray source is a copper tube ($\lambda \text{CuK}_{\alpha 1}$=1.54056 Å). The mounting comprises a front monochromator (Ge(111) crystal) and an energy-resolved solid-state detector (MXP-D1, Moxtec-SEPH).

The compound is well crystallised: the ray width at half-height is of the order of 0.07° (2θ). The following parameters were thus determined:

monoclinic crystal lattice lattice parameters: a=20.0903 Å, b=9.3194 Å, c=15.4796 Å, β=108.667° space group : $P2_1/n$ number of molecules in the unit cell: 8 unit cell volume: $V_{unit\ cell}$=2746.742 Å$^3$ density: d=1.13 g/cm$_3$

EXAMPLE 4

Pharmaceutical Composition

| Formulation for the preparation of 1000 tablets each containing a dose of 25 mg: | |
|---|---|
| Compound of Example 3 | 25 g |
| Lactose monohydrate | 62 g |
| Magnesium stearate | 1.3 g |
| Maize starch | 26 g |
| Maltodextrines | 9 g |
| Silica, colloidal anhydrous | 0.3 g |
| Sodium starch glycolate type A | 4 g |
| Stearic acid | 2.6 g |

EXAMPLE 5

Pharmaceutical Composition

| Formulation for the preparation of 1000 tablets each containing a dose of 25 mg: | |
|---|---|
| Compound of Example 3 | 25 g |
| Lactose monohydrate | 62 g |
| Magnesium stearate | 1.3 g |
| Povidone | 9 g |
| Silica, colloidal anhydrous | 0.3 g |
| Sodium cellulose glycolate | 30 g |
| Stearic acid | 2.6 g |

We claim:

1. A crystalline form II of agomelatine of formula (I):

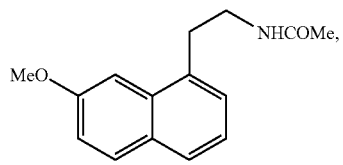

having a powder X-ray diffraction diagram exhibiting peaks at 6.30, 9.26, 10.50, 12.65, 13.29, 15.34, 15.81, 17.15, 18.03, 18.60, 19.01, 20.09, 20.44, 20.97, and 21.18 deg 2 theta.

2. A pharmaceutical composition comprising as active ingredient, an effective amount of the compound of claim 1, in combination with one or more pharmaceutically acceptable, inert, non-toxic carriers.

3. A method for treating a living animal body, including a human, afflicted with condition selected from anxiety and severe depression, comprising the step of administering to the living animal body, including a human, an amount of the compound of claim 1 which is effective for treatment of the condition.

* * * * *

UNITED STATES PATENT AND TRADEMARK OFFICE
CERTIFICATE OF CORRECTION

PATENT NO. : 7,498,465 B2  
APPLICATION NO. : 11/807941  
DATED : March 3, 2009  
INVENTOR(S) : Jean-Claude Souvie et al.

Page 1 of 1

It is certified that error appears in the above-identified patent and that said Letters Patent is hereby corrected as shown below:

Column 12, Line 22: "with condition" should be --with a condition--.

Signed and Sealed this

Twenty-second Day of September, 2009

David J. Kappos  
*Director of the United States Patent and Trademark Office*